United States Patent
Takiguchi

(10) Patent No.: US 7,797,999 B2
(45) Date of Patent: *Sep. 21, 2010

(54) MARKER DETECTION APPARATUS AND MARKER DETECTION METHOD

(75) Inventor: Kiyoaki Takiguchi, Kanagawa (JP)

(73) Assignee: Sony Corporation, Tokyo (JP)

( * ) Notice: Subject to any disclaimer, the term of this patent is extended or adjusted under 35 U.S.C. 154(b) by 357 days.

This patent is subject to a terminal disclaimer.

(21) Appl. No.: 11/875,411

(22) Filed: Oct. 19, 2007

(65) Prior Publication Data

US 2008/0092655 A1  Apr. 24, 2008

(30) Foreign Application Priority Data

Oct. 23, 2006 (JP) .......................... P2006-287899

(51) Int. Cl.
G01N 21/00 (2006.01)

(52) U.S. Cl. ......................................... 73/584; 356/338
(58) Field of Classification Search ................... 73/584, 73/658; 356/338
See application file for complete search history.

(56) References Cited

U.S. PATENT DOCUMENTS

| | | | |
|---|---|---|---|
| 5,641,457 A | 6/1997 | Vardanega et al. | |
| 7,381,565 B2 * | 6/2008 | Kurabayashi et al. | 436/63 |
| 2004/0260157 A1 * | 12/2004 | Montes | 600/301 |
| 2006/0021437 A1 | 2/2006 | Kaduchak et al. | |
| 2006/0088946 A1 * | 4/2006 | Willson et al. | 436/524 |

FOREIGN PATENT DOCUMENTS

JP  09-508703  9/1997

OTHER PUBLICATIONS

B. C. Towe, Ph.D., "Use of Piezoelectric Materials as Markers in Ultrasound Imaging", Proceedings of the First Joint BMES/EMBS Conference Serving Humanity, Advancing Technology, p. 1063 (1999).
European Search Report in EP 07 25 4186, dated Dec. 10, 2009.

* cited by examiner

*Primary Examiner*—Hezron Williams
*Assistant Examiner*—Nashmiya S Fayyaz
(74) *Attorney, Agent, or Firm*—Finnegan, Henderson, Farabow, Garrett & Dunner, L.L.P.

(57) ABSTRACT

A marker detection apparatus detects a marker attached to a target sample from samples flowing in a sample flow, wherein the sample flow carries a low ionization-tendency metal fine particle selected from a group of Au to Ag and the target sample labeled by the marker that is a particle of a unique vibration frequency, the marker detection apparatus including: an electromagnetic wave applying section that applies an electromagnetic wave to a path of the sample flow under a condition that the radius of the metal fine particle is smaller than the wavelength of the electromagnetic wave; and a detection section that detects vibration of the particle attached to the target sample, the vibration arising from a quasi-electrostatic field generated on the surface of the metal fine particle when the electromagnetic wave is applied to the metal fine particle around the target sample in the sample flow.

7 Claims, 8 Drawing Sheets

| TARGET SAMPLE | MARKER ATTACHED TO SAMPLES | | | CHARGE VOLTAGE |
|---|---|---|---|---|
| $C_1$ | $f_1$ | | | $VG_1$ |
| $C_2$ | | $f_2$ | | $VG_2$ |
| $C_3$ | $f_1$ | | $f_3$ | $VG_3$ |
| ⋮ | | | | ⋮ |
| $C_N$ | $f_1$ | $f_2$ | $f_4$ | $VG_N$ |

MARKER DETECTION APPARATUS AND MARKER DETECTION METHOD

CROSS REFERENCES TO RELATED APPLICATIONS

The present invention contains subject matter related to Japanese Patent Application JP2006-287899 filed in the Japanese Patent Office on Oct. 23, 2006, the entire contents of which being incorporated herein by reference.

BACKGROUND OF THE INVENTION

1. Field of the Invention

The present invention relates to a marker detection apparatus and marker detection method, and is preferably applied to a flow cytometry technique, or example.

2. Description of the Related Art

There are methods to retrieve a target living cell from various cells, and one of them is flow cytometry. Flow cytometry uses a flow or stream that carries a target sample labeled by a fluorescent substance or a marker. A laser beam is directed onto the flow at a right angle.

In the flow cytometry technique, after emitting the laser beam to the target sample, a specific wavelength of scattered and fluorescent light, separated by optical components, is picked up by a detector for measurement (see Jpn. Pat. Laid-open Publication H9-508703).

SUMMARY OF THE INVENTION

However, in the above flow cytometry technique, the laser beam is emitted in a direction perpendicular to the flow. If the marker exists behind the direction of emission of the laser beam, the detector may fail to detect the marker, resulting in decreased accuracy of detection.

The present invention has been made in view of the above points and is intended to provide a marker detection apparatus and marker detection method that can accurately detect a marker.

In one aspect of the present invention, a marker detection apparatus detects a marker attached to a target sample from samples flowing in a sample flow, wherein the sample flow carries a low ionization-tendency metal fine particle selected from a group of Au to Ag and the target sample labeled by the marker that is a particle of a unique vibration frequency, the marker detection apparatus including: an electromagnetic wave applying section that applies an electromagnetic wave to a path of the sample flow under a condition that the radius of the metal fine particle is smaller than the wavelength of the electromagnetic wave; and a detection section that detects vibration of the particle attached to the target sample, the vibration arising from a quasi-electrostatic field generated on the surface of the metal fine particle when the electromagnetic wave is applied to the metal fine particle around the target sample in the sample flow.

In that manner, the quasi-electrostatic fields are generated around the metal fine particles scattered around the target sample. Accordingly, even if the marker exists behind the direction of emission of the electromagnetic wave, the marker may get into the quasi-electrostatic fields and therefore the apparatus can detect the marker.

According to an embodiment of the present invention, using the quasi-electrostatic fields generated around the metal fine particles scattered around the target sample, the apparatus detects the vibration caused by the inverse piezoelectric effect of the particle attached to the target sample. Thus, the marker detection apparatus and marker detection method according to an embodiment of the present invention can accurately detect a marker.

The nature, principle and utility of the invention will become more apparent from the following detailed description when read in conjunction with the accompanying drawings in which like parts are designated by like reverence numerals or characters.

DETAILED DESCRIPTION OF PREFERRED EMBODIMENTS

An embodiment of the present invention will be described in detail with reference to the accompanying drawings.

(1) Overall Configuration of a Flow Cytometer

Figure 1:
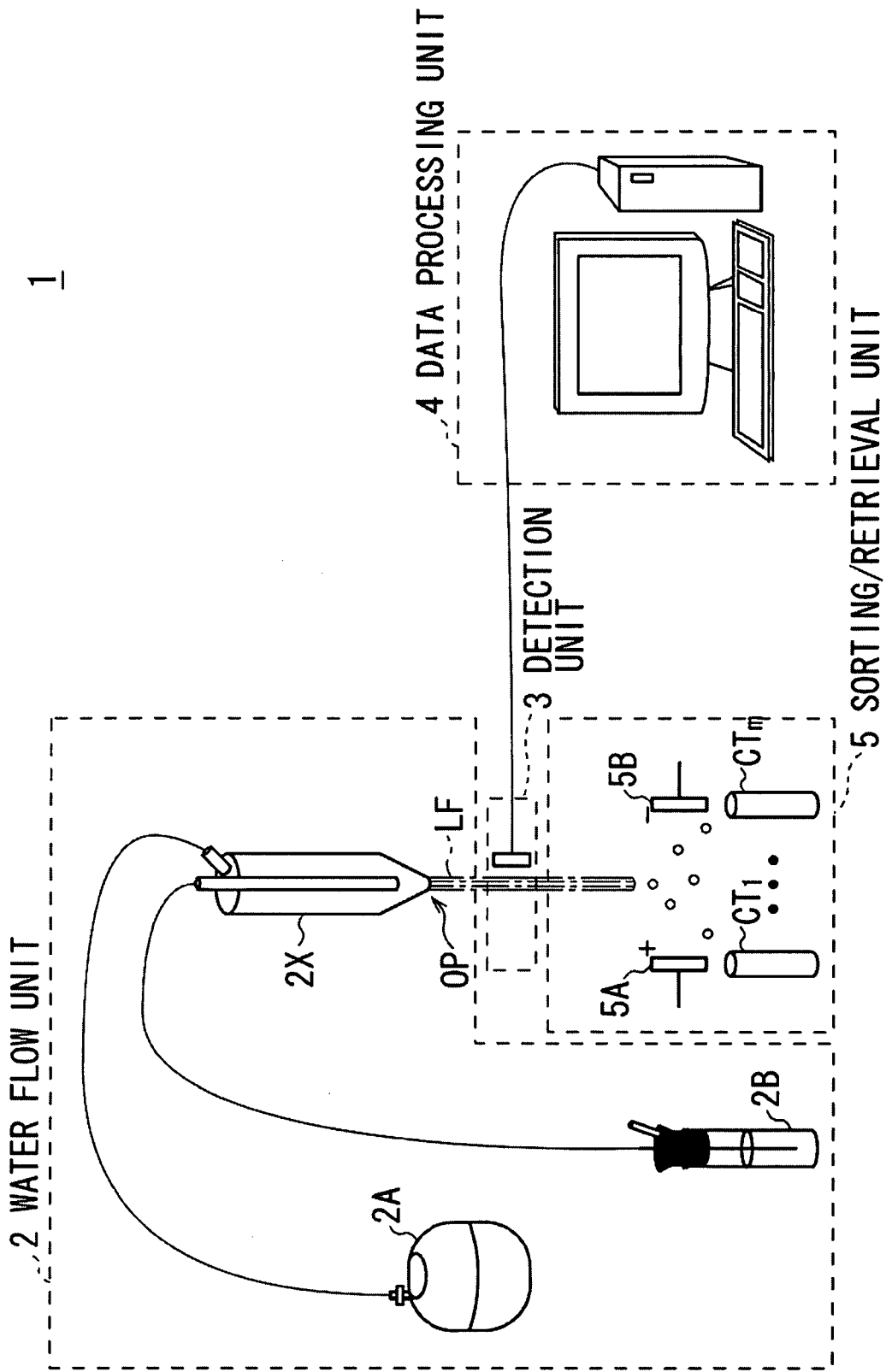
FIG. 1 is a schematic diagram illustrating the overall configuration of a flow cytometer according to an embodiment of the present invention.

FIG. 1 illustrates a flow cytometer according to an embodiment of the present invention. The flow cytometer 1 includes a water flow unit 2, a detection unit 3, a data processing unit 4 and a sorting/retrieval unit 5.

The water flow unit 2 includes a sheath flow generation section 2A that gives a predetermined sheath pressure to produce a sheath flow, which is then supplied via a sheath tube to an interflow chamber 2X. The water flow unit 2 also includes a sample flow generation section 2B that gives a predetermined sample pressure to generate a sample flow, which is then supplied via a sample tube to the interflow chamber 2X. As a result, the combined stream or layer flow LF spouts out from an outlet OP of a nozzle of the interflow chamber 2X, the sample flow being in the center of the combined stream while the sheath flow in the rim of the stream.

In line with the principle of Laminar Flow, the water flow unit 2 is designed to control the layer flow FL: The sample flow does not mix up with the sheath flow covering the sample flow and each sample flows separately in the sample flow.

The equation about the layer flow FL is defined as follows:

$$R = \frac{\rho a U}{\eta} \quad (1)$$

wherein "ρ" is fluid density of the layer flow LF, "a" is an inside diameter of the outlet OP (or the diameter of the layer flow), "U" is fluid velocity and "η" is fluid viscosity.

The layer flow FL is turbulent when R>1000. On the other hand, the layer flow FL is stable when R<1000. Such a state of the layer flow FL with R<1000 is known as laminar flow. Since fluid viscosity largely depends on temperature, the sheath flow generation section 2A appropriately controls temperature for the sheath flow.

The detection unit 3 is placed in the path of the layer flow. By using a quasi-electrostatic field, the detection unit 3 electrically detects a marker (label substance) attached to target samples, each of which separately exists in the sample flow. The detection unit 3 subsequently supplies resulting detection data to the data processing unit 4.

The data processing unit 4 is a computer to identify the type of the target sample from the detection data. After identifying the type, the data processing unit 4 decides how much charge voltage it will apply to the target sample.

The sorting/retrieval unit 5 applies the charge voltage, determined by the data processing unit 4, to the sample flow when the layer flow LF breaks into droplets (break off point). As a result, the charged droplet including the target sample is broken off from the layer flow LF by a positive deflection plate 5A with a predetermined voltage and a negative deflection plate 5B with a predetermined voltage, flowing into one of collection tubes $CT_1$ to $CT_m$ (m=2, 3 . . . ).

In that manner, the flow cytometer 1 identifies and sorts out the target sample.

(2) Marker

The following describes the marker attached to the target samples. The marker is used to identify the sample.

The marker used in this embodiment is a piezoelectric substance of a unique vibration frequency, including a piezoelectric crystal, a piezoelectric ceramics, a piezoelectric thin film, a piezoelectric polymer substance and a ferrodielectric substance (also known as relaxor).

The piezoelectric substance can be: crystal ($SiO_2$), lithium niobate ($LiNbO_3$), barium titanate ($BaTiO_3$), lead titanate ($PbTiO_3$), lead zirconate titanate (PZN), lead metaniobate ($PbNb_2O_6$), polyvinylidene fluoride (PVDF) and zinc oxide (ZnO).

The piezoelectric substance also can be: lithium tantalite ($LiTaO_3$), potassium niobate ($K_4NbO_3$), lithium tetraborate ($Li_2B_4O_7$), langasite ($La_3Ga_5SiO_{14}$), aluminum nitride (AlN) and tourmaline.

The method of attaching the marker (i.e. piezoelectric substance) to a target sample is: attaching the piezoelectric substance to a probe that is specific to a distinctive part of the target sample and then attaching the probe with the piezoelectric substance to the distinctive part of the target sample.

The probe can be an antibody. This kind of probe is used to detect a certain cell because an antibody is attached to the corresponding antigen by the primary antibody method, the secondary antibody method or affinity of avidin/biotin.

The probe may also include Annexin V, and MHC class I-peptide tetramer and the like. They are a high molecular weight protein of the immunoglobulin superfamily, used for detecting apoptotic cells or antigen-specific $CD8^+T$ cells.

In addition, there are probes, such as DNA oligomer or RNA oligomer, which utilizes characteristic of complementary binding of DNA and RNA. Those probes are used to detect the sequences of DNA or RNA because they attach to a specific sequence by hybridization.

On the other hand, there are methods to attach the piezoelectric substance to the probes. One of the methods is directly attaching the piezoelectric substance to the probes. The other is attaching the piezoelectric substance to the probes through organic polymeric materials such as dextran, albumin, starch, polyacrylamide and polyethylene glycol (refer to: Inada Yuji, protein hybridization Vol. 3, Kyoritsu Shuppan Co., Ltd. 1990).

Figure 2:
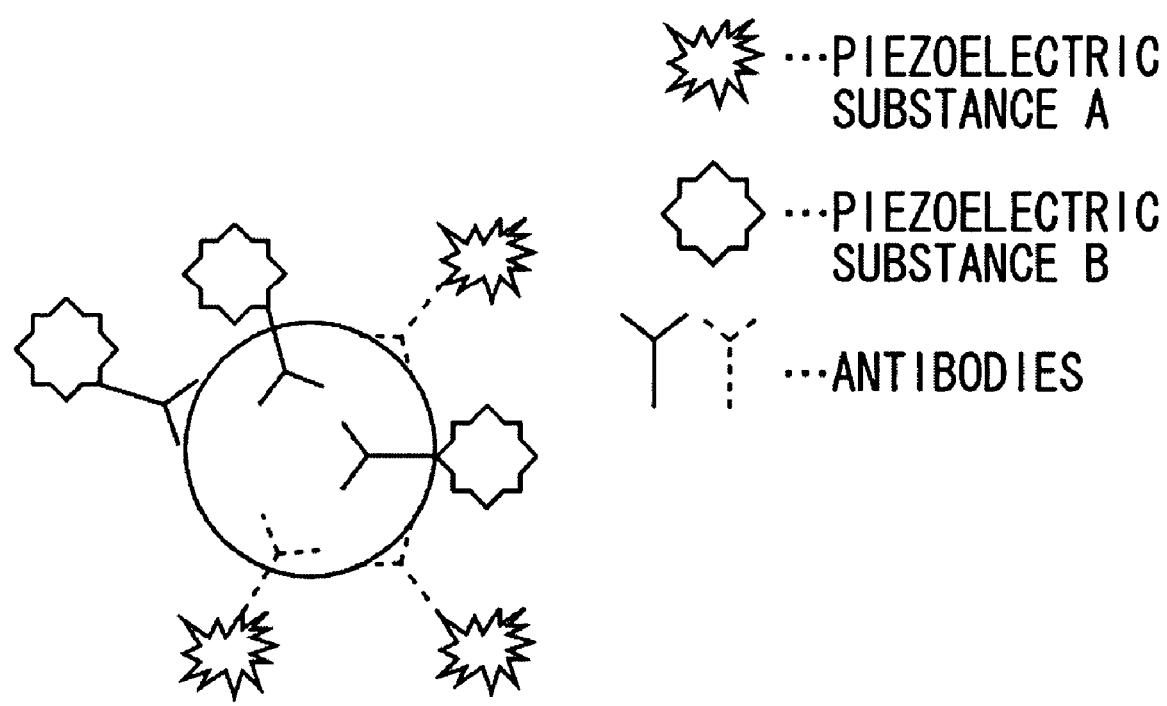
FIG. 2 is a schematic diagram illustrating piezoelectric substances attached to a target cell.

By the way, if two or more markers are used for detecting a target cell, each of them may be a piezoelectric substance of a different vibration frequency to be attached to the target cell. For example, when there is a target sample with two specific antigens as shown in FIG. 2, the piezoelectric substances (A and B), each of which has a different vibration frequency, are attached to the antigens through corresponding antibodies or probes. In this manner, one or more unique piezoelectric substances are attached to the target sample.

Figure 3:
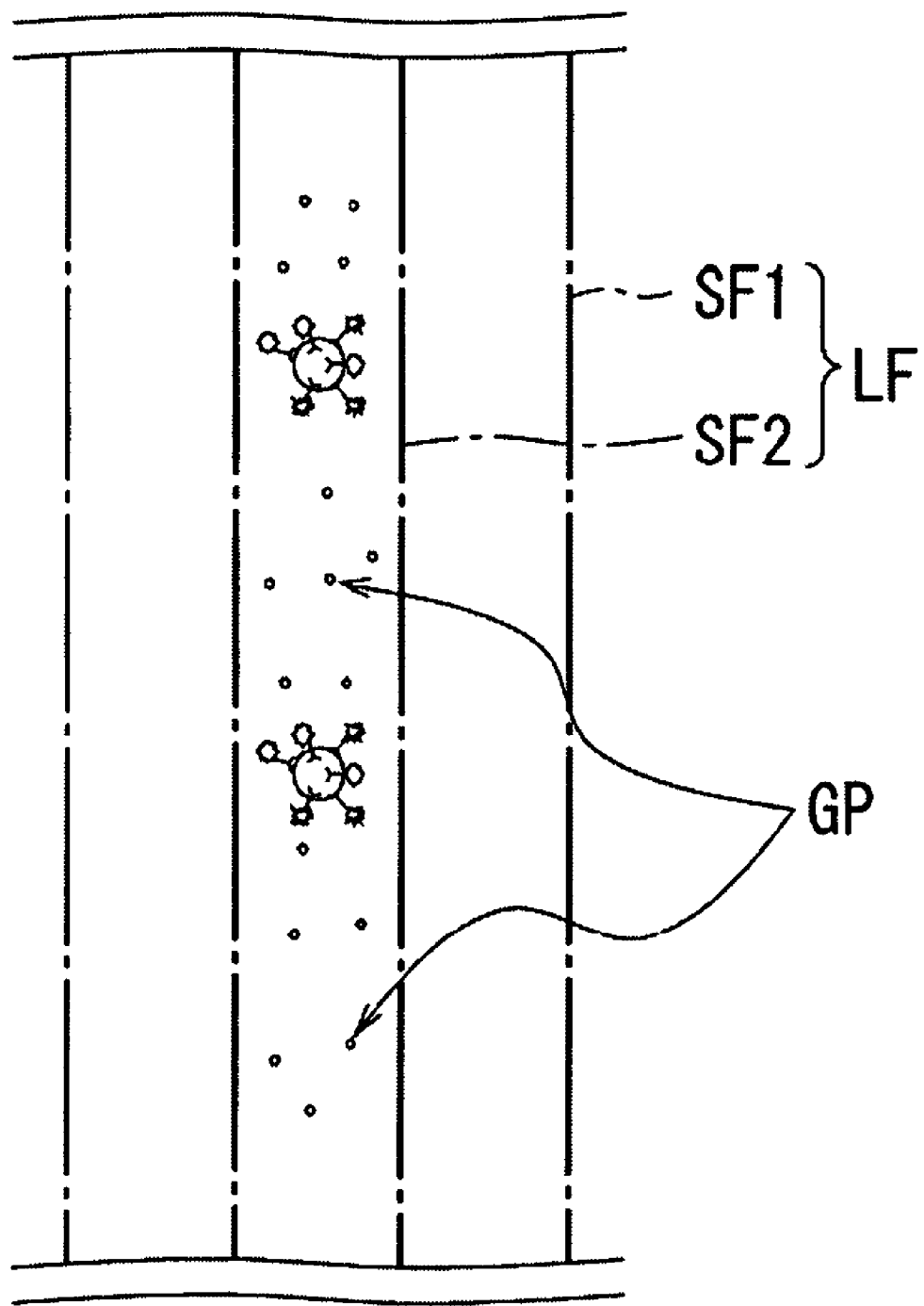
FIG. 3 is a schematic diagram illustrating gold fine particles and target cells flowing in a sample flow.

In this embodiment, the target samples, labeled by the markers, are put into solution (such as normal saline solution) along with gold fine particles. The solution is poured into the sample flow generation section 2B of the water flow unit 2. Accordingly, as shown in FIG. 3, the sample flow SF2, the center stream of the layer flow LF, includes the target cell and a plurality of gold fine particles GP around the cells.

(3) Configuration of the Detection Unit

Figure 4:
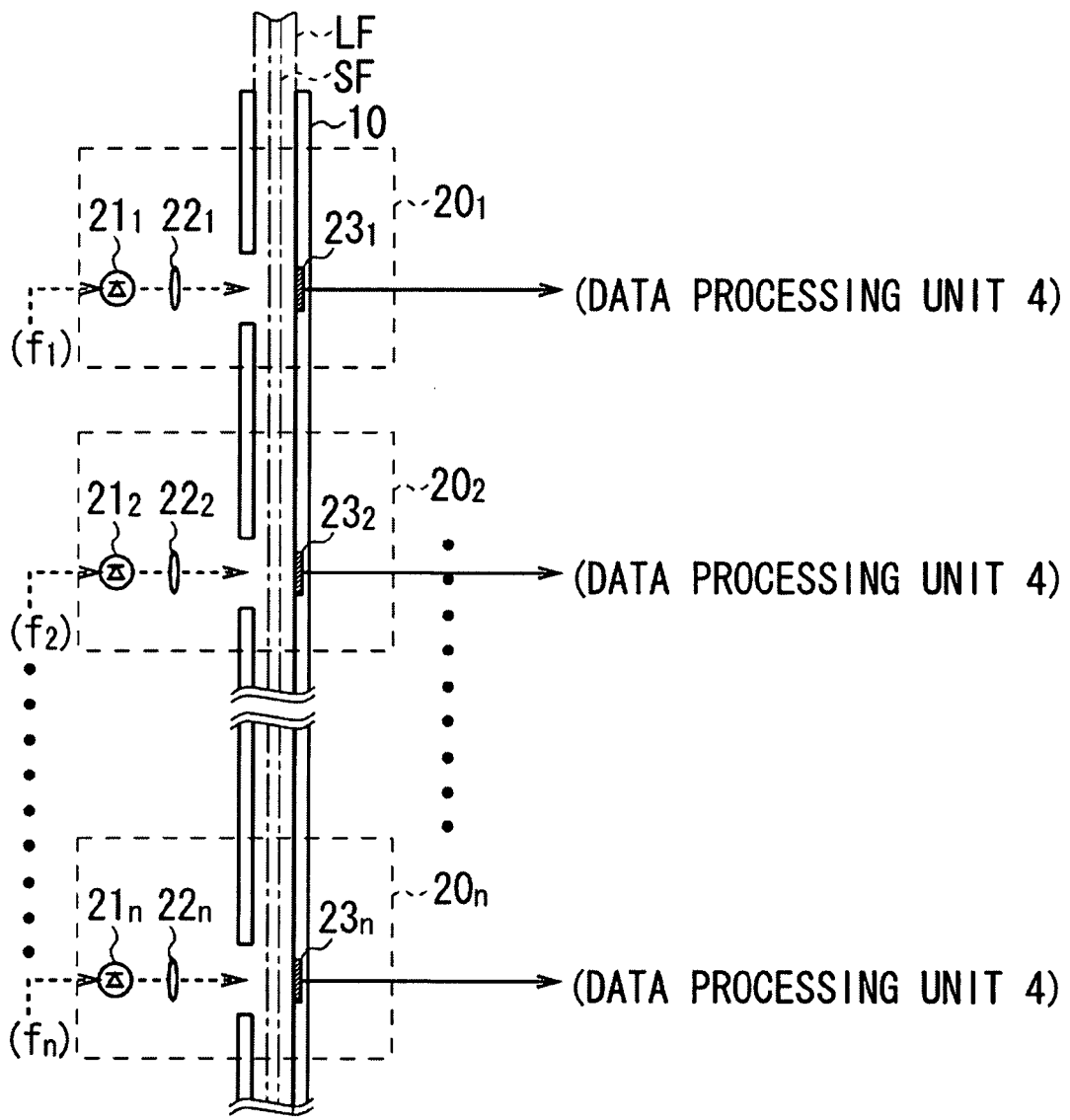
FIG. 4 is a schematic diagram illustrating the configuration of a detection unit.

Following describes the detection unit 3. As shown in FIG. 4, the detection unit 3 includes a layer flow tube 10 and a plurality of marker detection sections $20_1$ to $20_n$.

The layer flow tube 10 is connected to the interflow chamber 2X of the water flow unit 2. The layer flow tube 10 is placed as if the inner surface of the layer flow tube 10 covers the outer layer (i.e. the sheath flow SF1) of the layer flow LF emerging from the outlet OP of the nozzle of the interflow chamber 2X.

The marker detection sections $20_1$ to $20_n$ (n=2, 3 . . . ) include: laser beam sources $21_1$ to $21_n$ for emitting laser beams; optical components $22_1$ to $22_n$ for adjusting the direction of the laser beams so that they travel in a direction perpendicular to the sample flow SF2 of the layer flow LF; and elastic wave detection sections $23_1$ to $23_n$.

Figure 5:
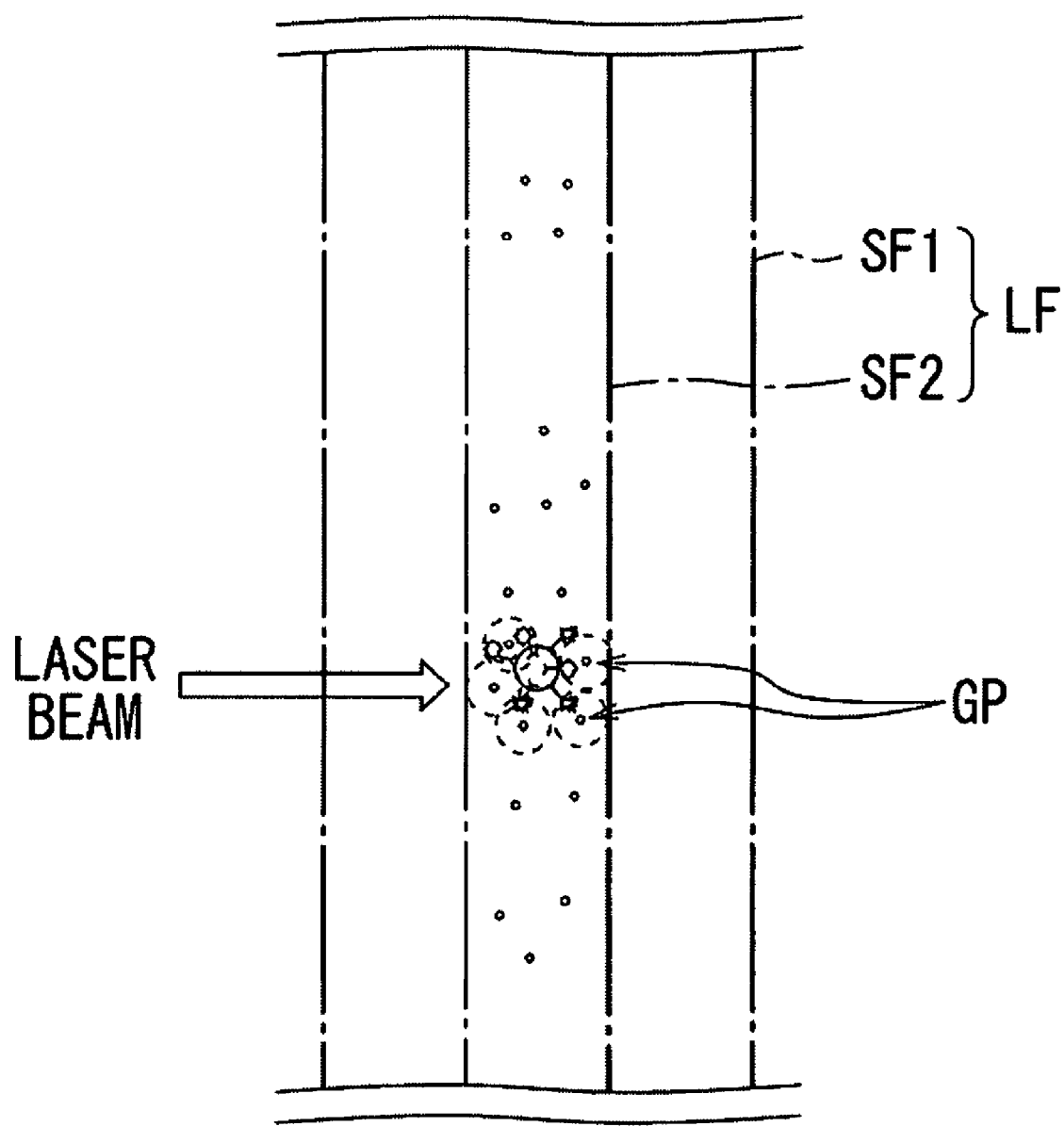
FIG. 5 is a schematic diagram illustrating a quasi-electrostatic field (near field) around the surface of the gold fine particles.

The laser beams are emitted from the laser beam sources $21_1$ to $21_n$ via the optical components $22_1$ to $22_n$ toward the sample flow of the layer flow LF. If the wavelength of the laser beams is larger than the diameter of the gold fine particles GP (FIG. 3) in the sample flow, the laser beams collide with the gold fine particles GP, generating a quasi-electrostatic field (i.e. a near field) inside a certain area of the surface of the gold fine particles GP, as shown in FIG. 5.

The laser beams are set at the same frequencies ($f_1$ to $f_n$) as the vibration frequencies of the piezoelectric substances (out of a plurality of piezoelectric substances of different vibration frequencies), which are associated with the target samples.

In this case, the sample flow SF2 carries the target sample labeled by the piezoelectric substance of a certain vibration frequency. When the target sample reaches an area to which the laser beam of the same frequency as the piezoelectric substance is emitted and then the target sample's piezoelectric substance gets into the quasi-electrostatic field (near field) around the gold fine particles GP, the piezoelectric substance begins to vibrate in a specific frequency (i.e. inverse piezoelectric effect). The elastic wave detection sections $23_1$ to $23_n$ detect its vibration distortion as elastic waves.

By the way, the elastic waves do not interfere with the charge voltage, which is applied to the sample flow SF2 by the sorting/retrieval unit 5, because the frequency of the elastic waves is different from that of the charge voltage.

Figure 6:
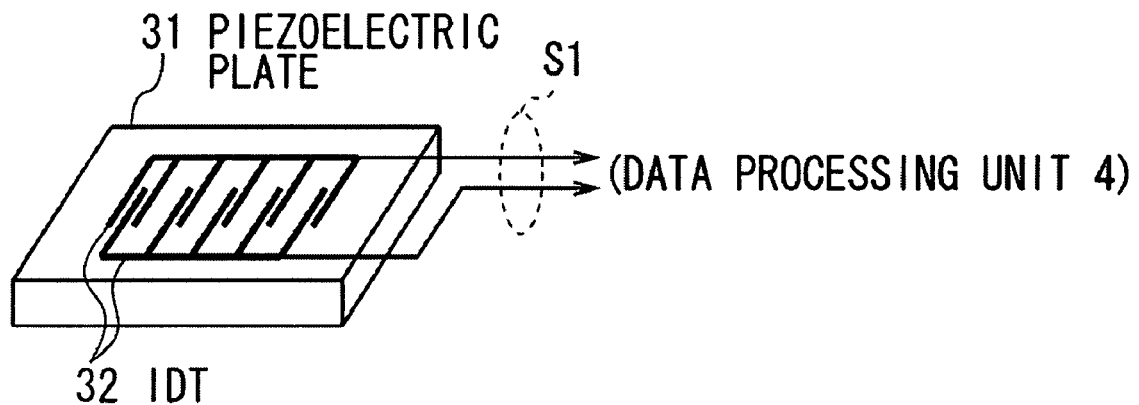
FIG. 6 is a schematic diagram illustrating an elastic wave detection section.

The elastic wave detection sections $23_1$ to $23_n$ are placed on the same plane as the area to which the laser beams are emitted. In addition, the elastic wave detection sections $23_1$ to $23_n$ are placed between the outer and inner surfaces of the layer flow tube 10 (FIG. 4). As shown in FIG. 6, each of the elastic wave detection sections $23_1$ to $23_n$ includes a piezoelectric plate 31 on which an Inter Digital Transducer (IDT) 32 is placed. The piezoelectric plate 31 will be in sympathetic vibration with the elastic waves from the target sample to generate a surface wave (i.e. piezoelectric effect).

The IDT 32 includes two comb-shaped conductors facing each other as if being interlocked, serving as a filter to extract a certain signal component. The signal component extracted by the IDT 32 varies due to the material of the piezoelectric plate and the interval of the teeth of the comb-like conductors. This can be represented as follows:

$$v = 2d \times f \quad (2)$$

wherein "v" is a propagation speed of the surface wave on the piezoelectric plate of the IDT32, "2d" represents the interval of the teeth of the comb-like conductors and "f" represents a center frequency of the IDT.

In this embodiment, the IDT 32 of the elastic wave detection sections uses a certain material for the piezoelectric plate with a certain interval regarding the teeth of the comb-like conductors such that they are suitable for the frequency of the laser beams emitted from the laser beam sources $21_1$ to $21_n$ (FIG. 4). Accordingly, the IDT 32 of the elastic wave detection sections retrieves a wave of the same frequency as the corresponding piezoelectric substance from the surface waves generated around the piezoelectric plate 31 and then supplies a resulting detection signal S1 to the data processing unit 4 (FIG. 1).

In that manner, the detection unit 3 has the light sources at certain intervals, which emit the laser beams of different frequencies to the sample flow SF2 and the gold fine particles inside the flow SF2, generating a quasi-electrostatic field around the gold fine particles. Accordingly, the piezoelectric substance attached to the target sample will be in sympathetic vibration around the area to which the laser beams are emitted. The elastic wave detection sections $23_1$ to $23_n$ detects the vibration and then supplies the resulting detection signal S1 (FIG. 6) to the data processing unit 4 (FIG. 1).

(4) Configuration of the Data Processing Unit

Figure 7:
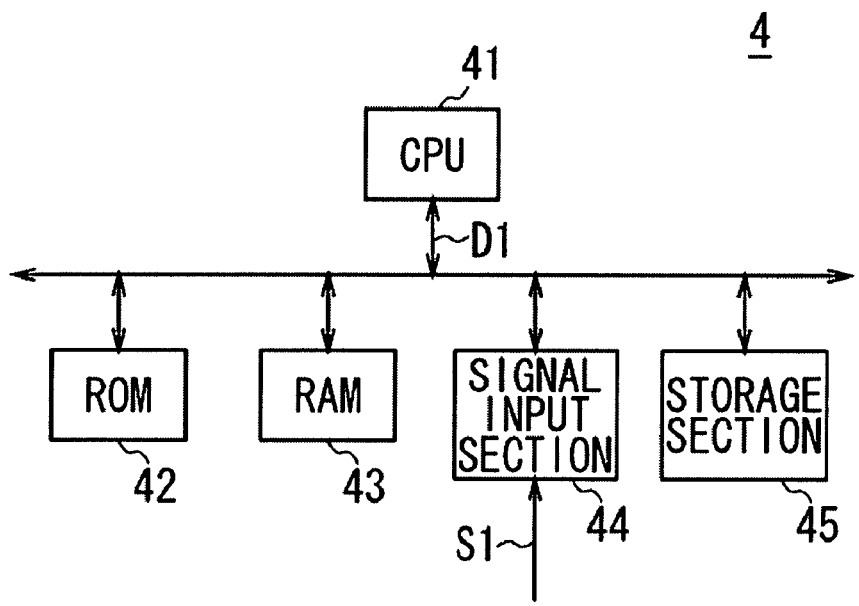
FIG. 7 is a block diagram illustrating the configuration of a data processing unit.

As shown in FIG. 7, the data processing unit 4 includes a Central Processing Unit (CPU) 41 connected to a Read Only Memory (ROM) 42, which stores various programs, a Random Access Memory (RAM) 43, which serves as a work memory for the CPU, a signal input section 44 and a storage section 45.

The signal input section 44 amplifies the detection signal S1, supplied from the IDT 32 (FIG. 6) of the elastic wave detection sections $23_1$ to $23_n$, and then performs an Analog-to-Digital (A/D) conversion process. The signal input section 44 subsequently supplies resultant detection data D1 to the CPU 41.

Figures 8, 9:
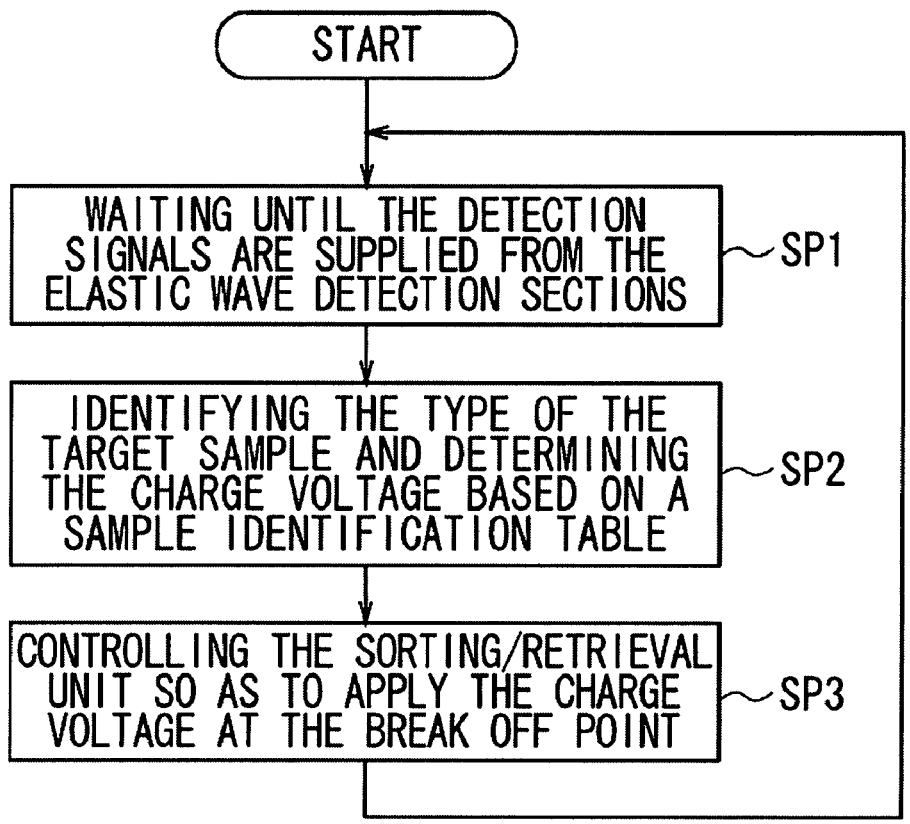
FIG. 8 is a schematic diagram illustrating a sample identification table.
FIG. 9 is a flowchart illustrating the procedure of an analyzing/sorting/retrieval process.

As shown in FIG. 8, the storage section 45 stores a database (also referred to as a "sample identification table") in which the types of the target samples, the condition of the markers (or piezoelectric substances) for the target samples and the values of the charge voltages applied to the target samples are associated with one another.

The CPU 41 executes a program stored in the ROM 42 and then identifies the type of the target sample in the sheath flow, based on the sample identification table and the detection data D1 from the signal input section 44. In addition, the CPU 41 determines how much charge voltage it will apply to the target sample.

FIG. 9 is a flowchart illustrating the process of the CPU 41. When receiving a process start command, the CPU 41 starts running the water flow unit 2, the detection unit 3 and the sorting/retrieval unit 5, and then proceeds to step SP1. At step SP1, the CPU 41 waits until it receives the detection signal S1 from the elastic wave detection sections $23_1$ to $23_n$.

After receiving the detection signal S1 from the elastic wave detection sections $23_1$ to $23_n$, the CPU 41 proceeds to step SP2. At step SP2, the CPU 41 identifies the type of the target sample that has passed through the elastic wave detection sections $23_1$ to $23_n$, based on the detection signal S1 and the sample identification table (FIG. 8) stored in the storage section 45. In addition, the CPU 41 determines how much charge voltage it will apply to the target sample.

Subsequently, the CPU 41 at step SP 3 notifies the sorting/retrieval unit 5 of the charge voltage level determined at step SP2 and then returns to step SP1. The sorting/retrieval unit 5 will apply that level of the charge voltage to the sample flow when the droplets break off the flow (break off point). As a result, the charged droplet including the target sample is broken off from the flow by the deflection plate 5A or 5B, flowing into one of collection tubes $CT_1$ to $CT_m$.

In that manner, the data processing unit 4 analyzes the target samples based on the detection result of the detection unit 3. In addition, the data processing unit 4 controls the sorting/retrieval unit 5 such that each collection tube CT collects a corresponding target sample.

(5) Operation and Effect

The flow cytometer 1 controls the laser beam source 21 to emit the laser beam to the layer flow LF in which there is gold fine particles GP whose radius is smaller than the wavelength of the electromagnetic wave.

The sample flow SF2, part of the layer flow LF, carries the gold fine particles GP having the lowest ionization tendency and the target samples labeled by the piezoelectric substance of a unique vibration frequency (FIG. 3). The flow cytometer 1 applies the laser beam to the gold fine particles GP in the sample flow SF2 to create a quasi-electrostatic field on the surface of the gold fine particles GP (FIG. 5) and then detects vibration of the particles.

In that manner, the flow cytometer 1 produces a quasi-electrostatic field (i.e. a near field) on a specific area of the surface of the gold fine particle GP around the target sample. Accordingly, even if the markers (or piezoelectric substances) exist behind the direction of the emitted laser beam, the quasi-electrostatic field may cover the gold fine particles GP, allowing the flow cytometer 1 to detect the target sample.

In addition to that, the quasi-electrostatic field is generated only on a specific area of the surface of the gold fine particles GP around the target sample. This may eliminate the effect of noise for precise detection.

The flow cytometer 1 includes a plurality of laser beam sources $21_1$ to $21_n$ and elastic wave detection section $23_1$ to $23_n$ to detect a plurality of piezoelectric substances of different vibration frequencies: One detection unit is a pair of a laser beam source 21 and an elastic wave detection section 23. Those detection units are spaced, along the layer flow, a predetermined distance away from each other so as to prevent the laser beams from the laser beam sources from affecting each other.

Accordingly, each detection unit detects a piezoelectric substance of a different vibration frequency. This enables the flow cytometer 1 to precisely detect the markers attached to the target sample even if there are various piezoelectric substances of different vibration frequencies as the markers of the target sample.

Moreover, the flow cytometer 1 according to the present embodiment can be downsized, compared to a typical laser-type flow cytometer that includes complex optical components for sorting out various types of scattered beams into corresponding detectors in order to detect the target samples labeled by various fluorescent markers.

Furthermore, the flow cytometer 1 has the layer flow tube 10 that carries the layer flow LF as if it covers the surface of the layer flow LF. Between the inner and outer surfaces of the layer flow tube 10 are placed the elastic wave detection sections 23 to make the elastic wave detection sections 23 close to the sample flow SF2. This allows the elastic wave detection sections 23 to precisely detect the vibration of the piezoelectric substances attached to the target samples. That also eliminates the effect of noise for precise detection.

According to the above configuration, the flow cytometer 1 can precisely detect the markers because it generates the quasi-electrostatic fields on the gold fine particles around the target samples for the inverse piezoelectric effect and then detects the vibration of the markers attached to the target samples.

(6) Other Embodiment

In the above-noted embodiment, the piezoelectric substances are used as markers. However, the present invention is not limited to this. The markers may include electrostrictive materials of certain vibration frequencies. The electrostrictive materials represents: When an electric field is applied to the crystal, the resulting strain will be proportional to the square of the polarization. The electrostrictive materials may be useful because there is no need for polarizing process for the electrostrictive materials (while the piezoelectric substance may need the polarizing process) and they have a symmetrical appearance.

Moreover, in the above-noted embodiments, the gold fine particles are used as a substance to be scattered around the target samples in the sample flow SF2. However, the present invention is not limited to this. That substance may include the low ionization-tendency materials like gold (Au) to silver (Ag), among the particles of Pt, Pd, Ag and the like. Especially, gold or platinum particles may be useful in terms of the safety for human being (such as examiners or mine workers) and the stability of the materials.

Furthermore, in the above-noted embodiments, the detection unit 3 includes: the layer flow tube 10, which carries the layer flow FL from the nozzle such that its inner surface covers the outer layer flow or the sheath flow SF1; the laser beam sources $21_1$ to $21_n$; the optical components $22_1$ to $22_n$ for adjusting the direction of the laser beams so that they travel in a direction perpendicular to the sample flow SF2 of the layer flow LF; and the elastic wave detection sections $23_1$ to $23_n$. However, the present invention is not limited to this. The detection unit 3 may be configured in a different manner.

Figure 10:
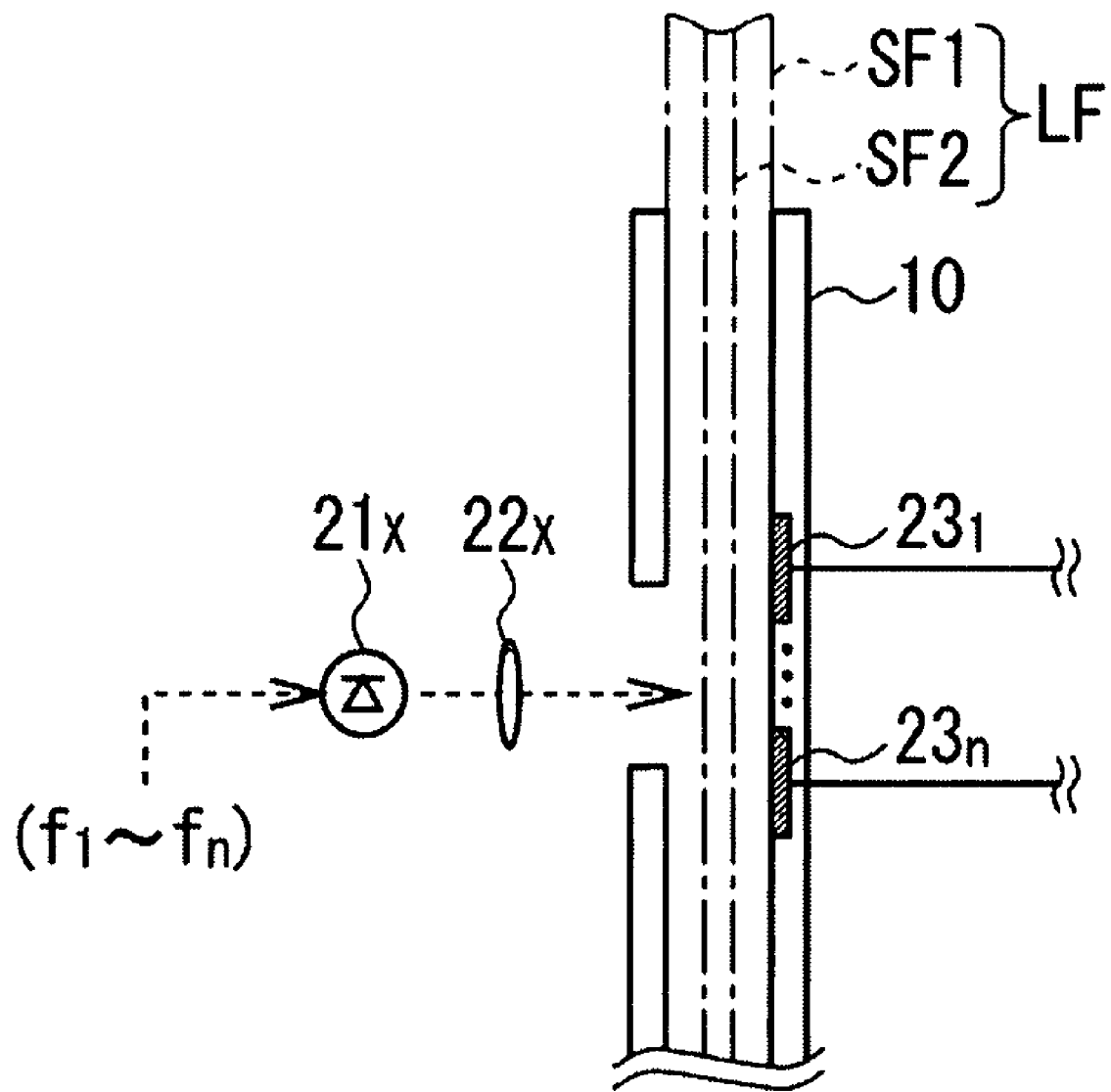
FIG. 10 is a schematic diagram illustrating a detection unit according to another embodiment of the present invention.

For example, FIG. 10 illustrates another configuration of the detection unit (the parts of FIG. 10 are represented as the same reference numerals and symbols as the corresponding parts of FIG. 4). Instead of the laser beam sources $21_1$ to $21_n$ (each of which emits a certain frequency of laser beam), the detection unit (FIG. 10) includes one laser beam source 21x to emit the laser beams of various frequencies, such as differential Gaussian pulse.

For example, in the detection unit (FIG. 10), the target samples reach the area where they receive the laser beams from the laser beam source 21x. When the piezoelectric substance attached to the target samples gets into the quasi-electrostatic fields (like FIG. 5) around the gold fine particles GP, the piezoelectric substance vibrates in its unique vibration frequency (i.e. inverse piezoelectric effect) and therefore the elastic wave detection sections $23_1$ to $23_n$ detect the vibration distortion as elastic waves.

If there are two or more markers (piezoelectric substances) attached to the target samples, each elastic wave detection section $23_1$ to $23_n$ detects a corresponding vibration frequency of piezoelectric substance and then generate the detection signal S1 (FIG. 6).

The detection unit (FIG. 10) allows the flow cytometer to be downsized because it has less number of laser beam sources to minimize the space for the layer flow tube 10. However, the elastic wave detection sections $23_1$ to $23_n$ may need to be placed in the quasi-electrostatic fields generated around the gold fine particles GP.

Instead of the differential Gaussian pulse, the detection unit (FIG. 10) may use, as the waves of various frequencies, surface transverse waves (STW), Rayleigh waves (SAW), SH surface waves (BGS wave: Bleustein-Gulyaev-Simizu wave), Lamb waves, Surface-Skimming waves, Shear Horizontal (SH) bulk waves and the like.

Furthermore, in the above-noted embodiment, the elastic wave detection sections 23 are used as detection means for detecting vibration of particles (such as piezoelectric or electrostrictive substances). However, the present invention is not limited to this. The detection section may include a piezoelectric plate and a band pass filter connected to the plate, as a Surface Acoustic Wave (SAW) device to detect a specific elastic wave or the vibration of the particle.

Furthermore, in the above-noted embodiments, the flow cytometer 1 applies electric charge (for a certain type of sample) to the sample flow SF2 and then the charged droplet including the target sample are broken off from the flow by the deflection plates 5A and 5B with predetermined positive and negative voltages at the break off point. However, the present invention is not limited to this. Alternatively, a predetermined charge voltage may be applied to the sample flow SF2 while the voltage applied to the deflection plates 5A and 5B changes according to the type of the target sample to attract the droplets including different samples in different ways.

The method according to an embodiment of the present invention can be applied to medicine production.

It should be understood by those skilled in the art that various modifications, combinations, sub-combinations and alterations may occur depending on design requirements and other factors insofar as they are within the scope of the appended claims or the equivalents thereof.

What is claimed is:

1. A marker detection apparatus for detecting a marker attached to a target sample from samples flowing in a sample flow, wherein
the sample flow carries a low ionization-tendency metal fine particle selected from a group of Au to Ag and the target sample labeled by the marker that is a particle made from a piezoelectric or electrostrictive substance of a unique vibration frequency, the marker detection apparatus comprising:
an electromagnetic wave applying section that applies an electromagnetic wave to a path of the sample flow under a condition that a radius of the metal fine particle is smaller than a wavelength of the electromagnetic wave; and
a detection section that detects vibration of the particle attached to the target sample, the vibration arising from a quasi-electrostatic field generated on a surface of the metal fine particle when the electromagnetic wave is applied to the metal fine particle around the target sample in the sample flow.

2. The marker detection apparatus according to claim 1, wherein:
the electromagnetic wave applying section applies to the path of the sample flow the electromagnetic wave having frequency components that correspond to vibration frequencies of a plurality of particles; and
a number of the detection sections correspond to a number of the vibration frequencies of the plurality of particles, the detection sections being provided along the sample flow.

3. A system comprising:
first and second marker detection apparatuses each for detecting a marker attached to a target sample from samples flowing in a sample flow, wherein
the sample flow carries a low ionization-tendency metal fine particle selected from a group of Au to Ag and the target sample labeled by the marker that is a particle made from a piezoelectric or electrostrictive substance of a unique vibration frequency, each of the marker detection apparatuses comprising:
an electromagnetic wave applying section that applies an electromagnetic wave to a path of the sample flow under a condition that a radius of the metal fine particle is smaller than a wavelength of the electromagnetic wave; and
a detection section that detects vibration of the particle attached to the target sample, the vibration arising from a quasi-electrostatic field generated on a surface of the metal fine particle when the electromagnetic wave is applied to the metal fine particle around the target sample in the sample flow, wherein;
the first apparatus and the second apparatus are provided along the sample flow to detect a plurality of particles of different vibration frequencies, each of the units including a pair of the electromagnetic wave applying section and the detection section; and
the detection sections are spaced a certain distance away from each other such that each of the detection section is not affected by the electromagnetic wave applying sections other than the corresponding electromagnetic wave applying section.

4. The marker detection apparatus according to claim 1, further comprising
a nonconducting tube that surrounds the sample flow, wherein
the detection section is provided between inner and outer walls of the tube.

5. The marker detection apparatus according to claim 1, wherein:
the detection section includes a piezoelectric plate and an Inter Digital Transducer (IDT) provided on the surface of the piezoelectric plate; and
a material of the piezoelectric plate and the shape of the IDT are determined such that the frequency of the electromagnetic wave applied by the electromagnetic wave applying section becomes equal to the center frequency of the IDT.

6. A marker detection method for detecting a marker attached to a target sample from samples flowing in a sample flow, wherein
the sample flow carries a low ionization-tendency metal fine particle selected from a group of Au to Ag and the target sample labeled by the marker that is a particle of a unique vibration frequency, the marker detection method comprising:
a first step of applying an electromagnetic wave to a path of the sample flow under a condition that a radius of the metal fine particle is smaller than the wavelength of the electromagnetic wave; and
a second step of detecting vibration of the particle attached to the target sample, the vibration arising from a quasi-electrostatic field generated on a surface of the metal fine particle when the electromagnetic wave is applied to the metal fine particle around the target sample in the sample flow.

7. A marker detection apparatus for detecting a marker attached to a target sample from samples flowing in a sample flow, wherein
the sample flow carries a low ionization-tendency metal fine particle selected from a group of Au to Ag and the target sample labeled by the marker that is a particle made from a piezoelectric or electrostrictive substance of a unique vibration frequency, the marker detection apparatus comprising:
means for applying an electromagnetic wave to a path of the sample flow under a condition that a radius of the metal fine particle is smaller than a wavelength of the electromagnetic wave; and
means for detecting vibration of the particle attached to the target sample, the vibration arising from a quasi-electrostatic field generated on a surface of the metal fine particle when the electromagnetic wave is applied to the metal fine particle around the target sample in the sample flow.

* * * * *